(12) United States Patent
Karuru et al.

(10) Patent No.: US 7,601,869 B2
(45) Date of Patent: Oct. 13, 2009

(54) PROCESS FOR THE PREPARATION OF FLORFENICOL

(75) Inventors: Mallikarjuna Reddy Karuru, Hyderabad (IN); Arun Kumar Gupta, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 104 days.

(21) Appl. No.: 11/922,468

(22) PCT Filed: Jun. 12, 2006

(86) PCT No.: PCT/IB2006/001676

§ 371 (c)(1),
(2), (4) Date: Dec. 18, 2007

(87) PCT Pub. No.: WO2006/136919

PCT Pub. Date: Dec. 28, 2006

(65) Prior Publication Data

US 2009/0043131 A1   Feb. 12, 2009

(30) Foreign Application Priority Data

Jun. 20, 2005   (IN) .......................... 753/CHE/2005

(51) Int. Cl.
C07C 233/05 (2006.01)
C07C 231/02 (2006.01)
(52) U.S. Cl. .................. 564/212; 564/133; 564/134; 564/135; 564/211; 564/218; 564/223
(58) Field of Classification Search ................ 564/133, 564/134, 135, 211, 212, 218, 223
See application file for complete search history.

(56) References Cited

U.S. PATENT DOCUMENTS 5,567,844 A * 10/1996 Jommi et al. ............... 564/209
2005/0075506 A1 * 4/2005 Handa et al. ............... 548/229

OTHER PUBLICATIONS

Schumacher et al, J. of Organic Chemistry, vol. 55, 1990, 5291-5294.*

* cited by examiner

*Primary Examiner*—Shailendra Kumar
(74) *Attorney, Agent, or Firm*—Jay Akhave

(57) ABSTRACT

The present invention relates to a method for the preparation of Florfenicol from Fluoroamine compound, namely (1R, 2S)-1-[4-(methylsulfonyl)phenyl]-2-amino-3-fluoro-1-propanol (II), by reaction with dihaloacetic acid ester in an organic solvent in presence of an inorganic base.

6 Claims, No Drawings

PROCESS FOR THE PREPARATION OF FLORFENICOL

This application is a 371 of PCT/IB2006/001676, filed Jun. 12, 2006.

FIELD OF THE INVENTION

The present invention relates to an improved process for preparing Florfenicol.

BACKGROUND OF THE INVENTION

Florfenicol, the fluoro derivative of thiamphenicol, has the structure of Formula I

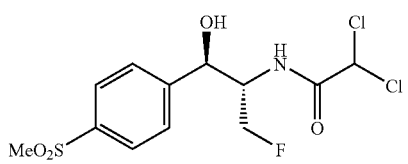

Florfenicol is a broad-spectrum antibiotic compound possessing activity against many Gram negative, Gram positive, and thiamphenicol-resistant microorganisms. Florfenicol, chemically known as (1R,2S)-2-dichloroacetamido-3-fluoro-1-[4-(methylsulfonyl)phenyl]-1-propanol, is of interest as a veterinary product.

Several prior-art references have described the process of preparing Florfenicol by acylating fluoro amine compound, (1R,2S)-1-[4-(methylsulfonyl)phenyl]-2-amino-3-fluoro-1-propanol (II) with dihaloacetatic acid ester as shown below:

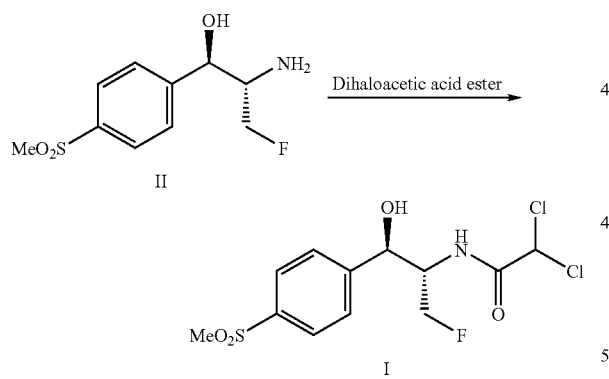

U.S. Pat. No. 4,235,892 describes a process of converting thiamphenicol into Florfenicol and other analogs. The process disclosed therein involves hydrolysis of thiamphenicol to produce aminodiol hydrochloride. Subsequently, amino group of aminodiol hydrochloride is protected with phthalic anhydride and fluorination is carried out to produce a phthalimido-fluoro alcohol. Thereafter, removal of the protecting group with hydrazine hydrate followed by acylation of the resulting fluoro amine compound with methyl dichloroacetate results in Florfenicol. This process does not provide Florfenicol of high purity and therefore further purification using column chromatography was carried out in the disclosed process.

U.S. Pat. No. 5,567,844 claims a process of acylation of Fluoro amine compound (II) with dihaloacetic acid in the presence of catalytic amounts of trialkylamine. However, this process is not exemplified in this reference.

Subsequently, *Journal of Organic Chemistry*, 55, 1990, 5291-5294, describes a commercial process for the production of Florfenicol wherein acylation of Fluoro amine compound (II) in methanol has been carried out with 5 mole equivalent of methyl dichloroacetate in presence of 1 mole equivalent of triethylamine. This acylation reaction has been accomplished by stirring for 18 hours at room temperature.

The acylation reaction of Fluoro amine compound (II) with dihaloacetic acid or with methyl dihaloacetate does not go to completion even after prolonged stirring and therefore extensive purification of Florfenicol is required to remove unreacted Fluoro amine. This results in lower yield, thereby adding on to the cost of Florfenicol.

In the instant invention, we have found that acylation of Fluoro amine compound with haloacetic acid ester can be conveniently carried out in presence of an inorganic base.

OBJECTIVE OF INVENTION

The main objective of the present invention is to provide an efficient and a simple process to produce Florfenicol (I) having high HPLC purity of greater than 99.5%.

SUMMARY OF THE INVENTION

Accordingly, the present invention relates to a method to convert Fluoro amine compound, namely (1R,2S)-1-[4-(methylsulfonyl)phenyl]-2-amino-3-fluoro-1-propanol (II) into Florfenicol (I) in an organic solvent by reacting with dihaloacetic acid ester in presence of an inorganic base.

The Reaction Scheme is as given below:

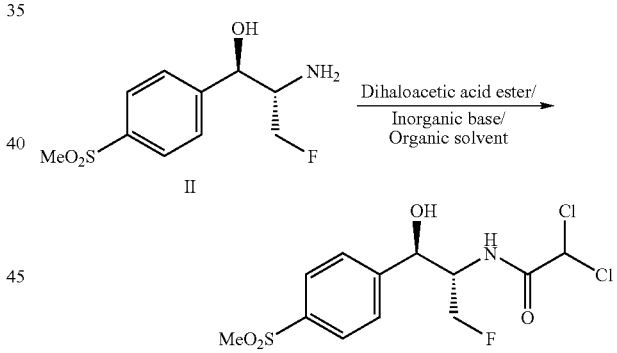

DETAILED DESCRIPTION OF THE INVENTION (1R,2S)-1-[4-(methylsulfonyl)phenyl]-2-amino-3-fluoro-1-propanol (II) is reacted with dihaloacetic acid ester in an organic solvent in the presence of an inorganic base to obtain Florfenicol (I), which is isolated by conventional methods known in literature.

The starting material, (1R,2S)-1-[4-(methylsulfonyl)phenyl]-2-amino-3-fluoro-1-propanol (II) is prepared by methods reported in chemical literature.

In an embodiment of the invention, (1R,2S)-1-[4-(methylsulfonyl)phenyl]-2-amino-3-fluoro-1-propanol (II) is acylated with dihaloacetic acid ester in presence of catalytic amount of an anhydrous inorganic base, selected from sodium carbonate, sodium bicarbonate, potassium carbonate, potassium bicarbonate and preferably in presence of anhydrous sodium carbonate in an organic solvent, selected from methanol, ethanol, 2-propanol, butanol etc and preferably in methanol. The reaction is carried out at 60-65° C. to accomplish the acylation in a shorter period of 2 to 4 hours. Further, these acylation conditions require 2 to 2.5 mole equivalent of methyl dichloroacetate for completion of the acylation reaction. After completion of the acylation, the solvent is distilled off under vacuum and the product is precipitated out by addition of toluene and water. The Florfenicol thus produced can be crystallized from aqueous organic solvent selected from methanol, ethanol, isopropanol, butanol etc and preferably from aqueous ethanol.

The major advantage realized in the process of the present invention is that the acylation is completed in 2 to 4 hours without using molar quantity of triethylamine. Further, it requires 2 to 2.5 mole equivalent of methyl dichloroacetate to complete the acylation reaction.

The invention is now illustrated with a non-limiting example, which is provided for illustrative purpose and is not to be construed to limit the scope of the invention.

EXAMPLE

Preparation of (1R,2S)-2-Dichloroacetamido-3-Fluoro-1-[4-(Methylsulfonyl)Phenyl]-1-Propanol (Florfenicol)

To a solution of (1R,2S)-1-[4-(methylsulfonyl)phenyl]-2-amino-3-fluoro-1-propanol (10 g, 0.04 mole) in methanol (100 ml) was added methyl dichloroacetate (14.48 g; 0.10 mole) and anhydrous sodium carbonate (0.43 g, 0.004 mole) and contents were heated to reflux at 60-65° C. for 2 hrs to complete the acylation reaction. After completion of the reaction, methanol was distilled off from the reaction mass under reduced pressure and Florfenicol was precipitated by addition of toluene (75 ml) and water (10 ml). The product was isolated by filtration, and dried. This was crystallized from 20% v/v aqueous ethanol to dive 11.50 g of Florfenicol having an HPLC purity of 99.73%.

We claim:
1. A process for the preparation of Florfenicol of Formula I,

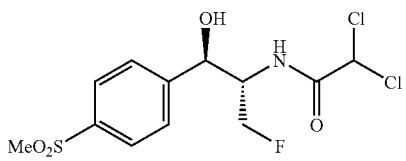

comprises reacting the Fluoro amine compound of Formula II

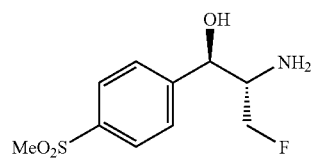

in an organic solvent with dihaloacetic acid ester in presence of an inorganic base.

2. The process as claimed in claim 1, wherein inorganic base is selected from sodium carbonate, sodium bicarbonate, potassium carbonate or potassium bicarbonate.

3. The process as claimed in claim 2, wherein the inorganic base is anhydrous sodium carbonate.

4. The process as claimed in claim 1, wherein the dihaloacetic acid ester is methyl dichloroacetate.

5. The process as claimed in claim 1, wherein organic solvent is methanol, ethanol, isopropanol, n-propanol or butanol.

6. The process as claimed in claim 5, wherein the organic solvent is methanol.

* * * * *